United States Patent [19]

Matsumura et al.

[11] Patent Number: 5,321,035
[45] Date of Patent: Jun. 14, 1994

[54] PIPERIDINE DERIVATIVES AND PROCESS FOR PREPARATION THEREOF

[75] Inventors: Hiromu Matsumura, Ashiya; Toshisada Yano, Kobe; Hiroshi Hashizume, Osaka; Nobuhiro Ibii, Kishiwada; Teruo Shiomi, Suzuka, all of Japan

[73] Assignee: Shionogi & Co., Ltd., Osaka, Japan

[21] Appl. No.: 93,950

[22] Filed: Jul. 21, 1993

[30] Foreign Application Priority Data

Jul. 23, 1992 [JP] Japan .................. 4-218152

[51] Int. Cl.$^5$ ............... A61K 31/545; C07D 401/12
[52] U.S. Cl. ................. 514/326; 546/208
[58] Field of Search ................. 546/208; 514/326

[56] References Cited

U.S. PATENT DOCUMENTS

| | | | |
|---|---|---|---|
| 4,476,308 | 10/1984 | Aschwanden | 546/208 |
| 4,977,167 | 12/1990 | Matsumura | 514/326 |
| 5,034,402 | 7/1991 | Aschwanden | 514/326 |
| 5,120,733 | 6/1992 | Matsumura | 514/252 |
| 5,149,817 | 9/1992 | Matsumura | 546/281 |
| 5,202,345 | 4/1993 | Matsumura | 514/423 |
| 5,243,051 | 9/1993 | Matsumura | 544/124 |

*Primary Examiner*—C. Warren Ivy
*Assistant Examiner*—Celia Chang
*Attorney, Agent, or Firm*—Wenderoth, Lind & Ponack

[57] ABSTRACT

A compound of the formula (I):

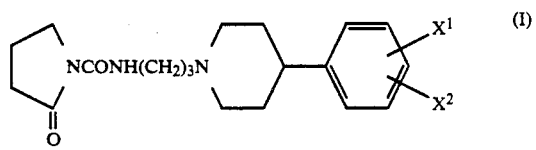

wherein $X^1$ nd $X^2$ each independently represents lower alkyl, lower alkoxy or halogen or a pharmaceutically acceptable salt thereof, which is useful as an active ingredient for a pharmaceutical composition for treating antidepressant or aftereffects of cerebrovascular impairments.

3 Claims, No Drawings

PIPERIDINE DERIVATIVES AND PROCESS FOR PREPARATION THEREOF

FIELD OF THE ART

The present invention relates to novel piperidine derivatives having pharmaceutically useful activities such as antidepressant and antiischemic activities and to a process for the preparation thereof.

BACKGROUND OF THE INVENTION

Recently, an increasing number of medicines for treating conditions or diseases caused by cerebral dysfunction or cerebral organic disorders including the disturbance of consciousness, disturbance of memory, dysgnosia, and various types of dementia have been developed. Examples of such medicine include consciousness disturbance improving agents, psychotropic agents, anti-, dementia agents, and the like. The present inventors have already developed and disclosed carbamoyl pyrrolidone derivatives effective on senile dementia (EP-A-0304330) and tetrahydropyridine derivatives having psychotropic activity (EP-A-0445701).

The present inventors have made a continuous and intensive research with the purpose of developing novel compounds that have the following properties:

(1) a potent inhibitory activity against re-uptake of serotonin;

(2) a potent ability to suppress or inhibit the delayed necrosis of neuronal cells; and (3) less or negligible enzyme induction. These properties will be explained in detail below.

(1) It has been well known that compounds capable of inhibiting the uptake of serotonin exhibit antidepressant activity (J. Clin. Psychiatry, 55: 3, March 1992). Thus, certain known antidepressants such as imipramine and amitriptyline are capable of inhibiting the amine pump responsible for the re-uptake of serotonin, which is released from the end of serotonergic nerves of central nervous system, by a neuroterminal, thereby increasing the serotonin concentration in the synaptic cleft.

(2) Cerebral ischemia is a local anemia of extremely high degree found in brain. Cerebral tissues placed under an ischemic condition often lead to dysfunction and, if the condition lasts, it would bring about the denature and necrosis of cells.

(3) In the clinical treatment with medicines, a gain in liver weight is observed following the administration of a medicine. This is due to the increase in the number of smooth surfaced endoplasmic reticulum (SER) in hepatic microsomes, which contains a series of enzymes participating in the drug metabolism. Thus, the administration of a medicine can stimulate the enzymatic activity which results in induction of enzymes responsible for the metabolism of drugs and shorten the term during which the medicine can exert its effect. The relationship between the enzyme induction and pharmacological and chemical structural features of a medicine has not been elucidated.

SUMMARY OF THE INVENTION

The present inventors, in view of the foregoing circumstances, have intensively studied and found that certain piperidine derivatives have the above-mentioned desirable properties, that is, (1) a potent inhibitory activity against the re-uptake of serotonin; and (2) a potent ability to suppress or inhibit the delayed necrosis, of neuronal cells, and (3) less or negligible enzyme induction.

Thus, the present invention provides a compound of the formula (I):

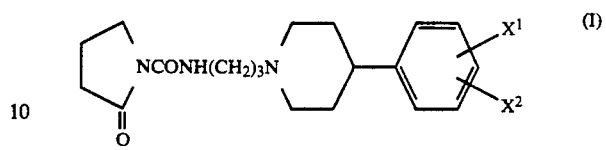

wherein $X^1$ and $X^2$ each independently represent lower alkyl, lower alkoxy or halogen, or a pharmaceutically acceptable salt thereof. The compounds of the present invention can be prepared, for example, by the process consisting of the following steps:

(1) a compound of the formula:

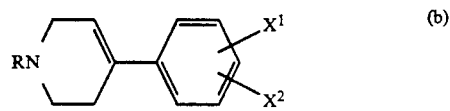

wherein $X^1, X^2$ are as defined above and R represents an amino-protecting group, is reduced, or (2) a compound of the formula:

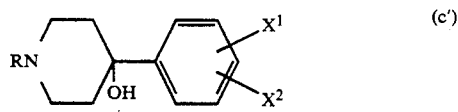

wherein $X^1$, $X^2$, and R are as defined above, is allowed to react with a trialkylsilane such as $Et_3SiH$ in the presence of an acid such as a Lewis acid, trifluoroacetic acid, and the like and, if necessary, deprotected to obtain a compound of the formula:

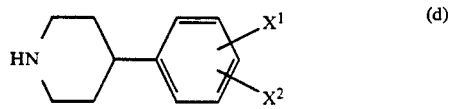

wherein $X^1$ and $X^2$ are as defined above, which is then allowed to react with 1-{3-(chloropropyl)carbamoyl}-2-oxopyrrolidine to obtain the ultimate compound of the formula (I). Accordingly, another object of the present invention is to provide a process for preparing the compound of the formula (I).

The compounds of the invention, which include the compounds of the formula (I) and pharmaceutically acceptable salts thereof, are extremely useful for the therapeutical treatment of depressant, dementia, and aftereffects of cerebrovascular disorders with negligible or only little reduction of therapeutical activity when it is administered continuously for a long term. The compound of the invention especially show an excellent inhibitory activity against the necrosis of neuronal cells due to the cerebral ischemia as well as an excellent antidepressant activity.

For purposes of the present invention, as disclosed and claimed herein, the following terms are defined below.

The term "lower alkyl" refers to a straight or branched $C_1$-$C_6$ alkyl group, including methyl, ethyl, n-propyl, isopropyl, n-butyl, isobutyl, sec-butyl, tert-butyl, n-pentyl, isopentyl, neopentyl, tert-pentyl, 2-methylbutyl, n-hexyl, isohexyl and the like.

The term "lower alkoxy" refers to a straight or branched $C_1$-$C_6$ alkoxy group, including methoxy, ethoxy, propoxy, butoxy, pentyloxy, hexyloxy and the like.

Examples of halogen include fluorine, chlorine, bromine and iodine.

Examples of pharmaceutically acceptable salts are those formed with inorganic acids such as hydrochloric acid, sulfuric acid, nitric acid, phosphoric acid and the like; or organic acids such as formic acid, acetic acid, propionic acid, succinic acid, fumaric acid, maleic acid, tartaric acid; citric acid, oxalic acid and the like. Preferable salts are those formed with oxalic acid and maleic acid.

DETAILED DESCRIPTION OF THE INVENTION

Although the compounds of the present invention can be prepared using any of known methods in the art, the process as illustrated below is preferable.

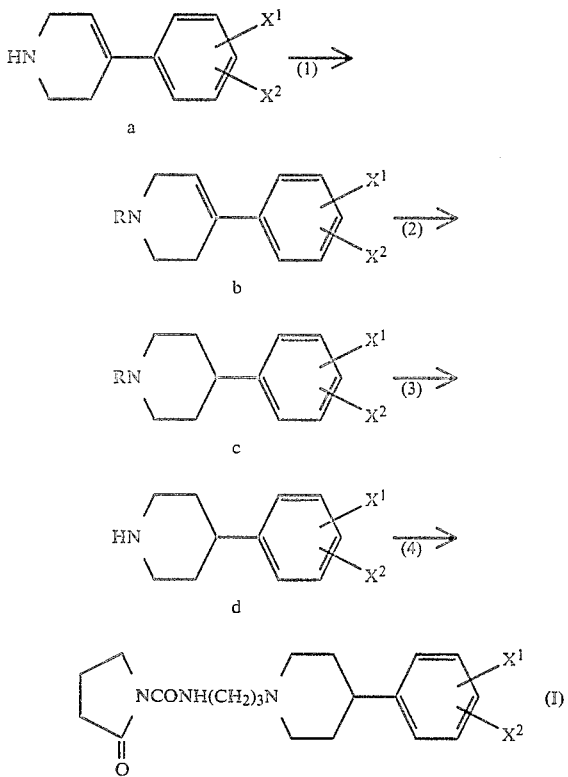

wherein $X^1$, $X^2$ and R are as defined above.

(1) The compound a is converted into the compound b by reacting it with an appropriate reagent in the presence of a base in a suitable solvent to protect the amino group of the tetrahydropyridine moiety of the compound a.

This reaction is carried out at 10–150° C., preferably around room temperature for 1–20 hr, more preferably 1–3 hr.

Examples of suitable solvents include organic solvents, for example, alcohols such as methanol, ethanol and the like; ethers such as diethyl ether, tetrahydrofuran and the like; dimethylformamide; acetonitrile; methylene chloride and the like.

Examples of bases include sodium hydroxide, potassium hydroxide, calcium hydroxide, potassium carbonate, pyridine, triethylamine and the like.

For purposes of the invention, any conventional amino protecting groups are available on conditions that they can be removed through other method than catalytic reduction. Examples of such amino protecting groups include acyl derivatives such as benzoyl, acetyl, formyl, trifluoroacetyl and the like; urethane-type derivatives such as benzyloxycarbonyl, tert-butoxycarbonyl, isopropoxycarbonyl, methoxycarbonyl, ethoxycarbonyl and the like; and alkyl derivatives such as allyl, benzyl, trityl, tetrahydropyranyl and the like. Tert-butoxycarbonyl is especially preferred.

(2) The compound b is subjected to hydrogenation in an appropriate organic solvent, preferably in the presence of a catalyst to yield the compound c. The reaction is carried out at 10–150° C, preferably around room temperature.

In this reaction, similar organic solvents as those illustrated in step (1) above can be used.

Conventional catalysts used for hydrogenation such as oxides or sulfides of a metal such as platinum, iron, nickel, copper and the like, are available. For the present invention, platinum oxide is especially preferred.

(b 3) Deprotection of the compound c by means of conventional procedures in the presence of trifluoroacetate/anisole provides the compound d. The reaction is carried out at 10–100° C, preferably around room temperature.

Alternatively, the compound d can be synthesized as follows.

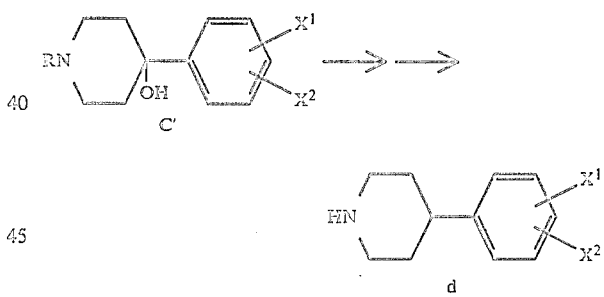

The compound c' (prepared in accordance with the method set forth in Japanese Patent Publication (Examined) No. 5266/1970) is first converted into the compound c by treating the former with a trialkylsilane such as $Et_3SiH$ in an appropriate solvent in the presence of a Lewis acid such as $AlCl_3$ at −50–150° C., preferably at temperature between ice-cold temperature and about room temperature, and the resultant compound c is further heated under the same conditions to yield the compound d.

In this process, organic solvents and bases similar to those illustrated in step (1) above are available. (4) The compound d is reacted with 1-{(3-chloropropyl)carbamoyl}-2-oxopyrrolidine in an appropriate solvent in the presence of a base to yield the compound (I). This reaction is carried out at 50–300° C., preferably 90–120° C. for 1–20 hr, more preferably 5–8 hr.

Appropriate solvents usable in the reaction are similar to those used in step (1). In the present reaction, dimethylformamide is preferred.

Examples of bases include potassium carbonate, sodium hydroxide, potassium hydroxide, calcium hydroxide, pyridine, triethylamine and the like. In the present process, potassium carbonate is most preferable.

The compound of the present invention can be orally or parenterally administered to human or animals. For the oral administration, it can be formulated into ordinary solid formulations such as tablets, powders, capsules, granules and the like; aqueous or oily suspensions; liquid formulations such as syrups, elixirs and the like. In the case of parenteral administration, a compound of the present invention may be formulated into an aqueous or oily suspension for injection. In preparing the formulations, conventional excipients, binders, lubricants, aqueous solvents, oily solvents, emulsifiers, suspending agents or the like may be used, and other additives, such as preservatives, stabilizers or the like may also be included.

Although appropriate daily dosage of the compound of the present invention varies depending upon the administration route, age, body weight and conditions of, a particular patient, and a particular disease to be treated, the daily dose for adult can generally vary between 5-1000 mg, preferably 20-200 mg, for oral administration, and 1-500 mg, preferably 5-50 mg, for parenteral administration. The daily dose can be administered in 1-5 divisions.

The following Example is provided to further illustrate the present invention and should not be construed as limiting the scope of the invention.

The abbreviations used in the Example have the following meanings: Boc=tert-butoxycarbonyl; and DMF=N, N-dimethylformamide.

EXAMPLE 1

1-[3-{4-(3,4-Dichlorophenyvl)piperidin-1-yl}propylcarbamoyl]-2-oxopyrrolidine (I)

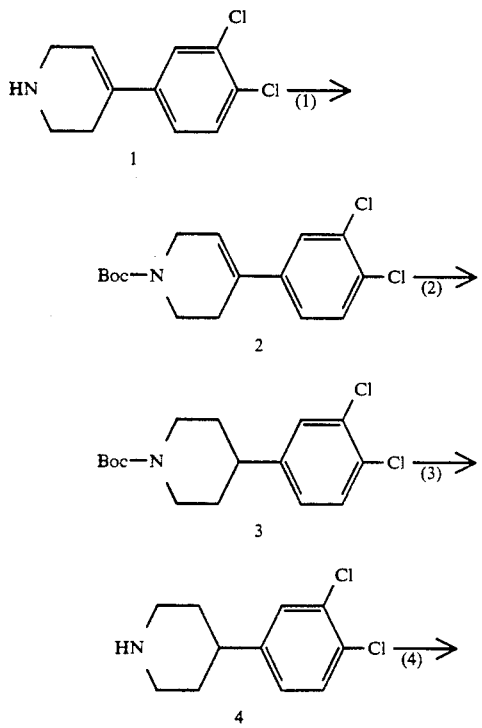

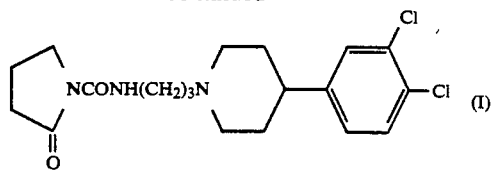

(1)
4-(3,4-Dichlorophenyl)-1-tert-butoxycarbonyl-1,3,6-tetrahydropyridine 2

A 13 ml solution of a mixture of compound 1 (1.49 g, 6.36 mM), di-tert-butoxycarbonyl anhydride (1.61 ml, 7.00 mM) and triethylamine (0.89 ml, 6.36 mM) in methylene chloride is stirred for 2 hr at room temperature. The reaction mixture is poured into ice-cold hydrochloric acid and the organic layer is separated. The remaining aqueous layer is extracted with methylene chloride. The resultant organic layers are combined, washed with water, dried over magnesium sulfate and concentrated. The residue is purified by a column chromatography on silica gel (toluene/ethyl acetate, 24:1) to yield the compound 2 (2.057 g; yield, 98.6 %) as a pale yellow oil. IR (CHCl$_3$) cm$^{-1}$:1680, 1550, 1423, 1364. NMR (CDCl$_3$) δ: 1.491 (s, 9H), 2.38-2.54 (m, 2H), 3.629 (t, J=6Hz, 2H), 4.073 (q, J=3Hz,2H), 6.055 (brs, 1H), 7.173, 7.215 (ABq, J=2Hz, 1H), 7.391 (d, J=8Hz, 1H), 7.442 (d, J=2Hz, 1H).

(2)
4-(3,4-Dichlorophenyl)-1-tert-butoxycarbonyl-1-piperidine 3

The compound 2 obtained above (3.331 g, 10.15 mM) is subjected to hydrogenation in methanol (50 ml) in the presence of platinum dioxide (398 mg) at room temperature. After removal of the catalyst and the solvent, the residue is poured into sodium bicarbonate solution followed by the extraction with methylene chloride. The organic layer is dried over magnesium sulfate and evaporated under vacuum. The residue is purified by a column chromatography on silica gel (toluene/ethyl acetate, 24:1) to yield the compound 3 (70 g; yield, 76.2 %) as a colorless oil. IR (CHCl$_3$) cm$^{-1}$:1673, 1471, 1463, 1437, 1422, 1361 NMR (CDCl$_3$) δ: 1.480 (s, 9H), 1.592 (t-d, J1=13Hz, J2=4Hz, 2H), 1.797 (d, J=11Hz, 2H), 2.51-2.71 (m, 1H), 2.783 (t-d, J1=12Hz, J2=2Hz, 2H), 4.244 (d, J=13Hz, 2H), 7.013,7.054 (ABq, J=2Hz, 1H), 7.287 (d, J=2Hz, 1H), 7.369 (d, J=8Hz,1H).

(3) 4-(3,4-Dichlorophenyl)piperidine 4

A 5 ml solution of a mixture of the compound 3 obtained above (2.709 g, 8.20 mM), trifluoroacetic acid (5 ml) and anisole (0.5 ml) in methylene chloride is stirred for 55 min at room temperature. After removal of the reagents and the solvent, the residue is poured into sodium bicarbonate solution and extracted with methylene chloride. The organic layer is dried over magnesium sulfate and evaporated under vacuum. The residue is purified by column chromatography on silica gel (methylene chloride/methanol/ammonia water, 128:16:1) to yield a maleic acid salt of compound 4 (1.12 g; yield, 59.2%) as a colorless oil. Recrystallization from methanol/ether gives, crystals of the maleate as a colorless plate.

M.p.=154.0-155.5° C.

| Analysis (%) for $C_{11}H_{13}Cl_2N.C_4H_4O_4$ |
|---|
| Calc.: C,51.84; H,4.96; N,4.13; Cl,20.40 |
| Found: C,52.04; H,4.95; N,4.05; Cl,20.48 |

IR (Nujol): 3261, 2770, 2710, 2575, 2485, 1701, 1638, 1618, 1574,1556(sh), 1522, 1478, 1463, 1448, 1378.

NMR (CD$_3$OD) δ:1.72–2.00 (m, 2H), 2.081 (d, J=14Hz, 2H), 2.81–3.03 (m, 1H), 3.130 (t-d, J1=13Hz, J2=3Hz, 2H), 3.507 (d, J=12Hz, 2H), 6.259 (s, 2H), 7.196, 7.237(ABq, J=2Hz, 1H), 7.453 (d, J=2Hz, 1H), 7.487 (d, J=8Hz, 1H).

(4) Alternative method for preparing 4-(3,4-dichlorophenyl)piperidine 4

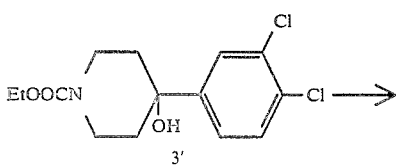

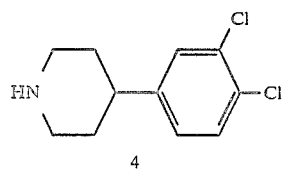

Et$_3$SiH (2.56 g, 22 mM) is dissolved in methylene chloride (5 ml) under ice-cooling, and AlCl$_3$ (2.1 g, 15.7 mM) is added to the resultant solution, and the mixture is stirred for 10 min. Subsequently, the compound 3'(1 g. 3.1 mM) (prepared in accordance with the method disclosed in GB-1141664, Preparation Example No. 2) dissolved in methylene chloride (20 ml) is dropwise added to the mixture under ice-cooling. After stirring for 50 min at the same temperature, the mixture is allowed to warm to room temperature and the stirring is continued for 5 hr. The reaction mixture is poured into an aqueous sodium bicarbonate solution, and precipitated Al(OH)$_3$ is filtered off by the use of Celite, and the filtrate is successively washed with water and saturated saline, dried over magnesium sulfate, and evaporated under vacuum to remove the solvent. The resultant residue is purified by column chromatography on silica gel (CHCl$_3$/MeOH/NH$_4$OH=128/16/1) to give the compound 4 as crystals (0.4 g; yield, 55%).

(5) 1-[3-{4-(3,4-Dichlorophenyl)piperidin-1-yl}-propylcarbamoyl]-2-oxopyrrolidine (I)

A mixture of the compound 4 obtained above (1.062 g, 4.61 mM), 1-{(3-chloropropyl)carbamoyl}-2-oxopyrrolidine (944 mg, 4.61 mM), potassium carbonate 1.238 g (9.22 mM), NaI (1.037 g, 6.92 mM) and DMF (15 ml) is stirred for 6.5 hr at 105° C. The reaction mixture is poured into ice-cold water and extracted with ethyl acetate. The organic layer is washed with water, dried over magnesium sulfate and evaporated under vacuum. The residue is purified by column chromatography on silica gel (methylene chloride/methanol/ammonia water, 128:12:1–128:16:1) to yield a hydrochloric acid salt of the compound (I) (1.415 g; yield, 77.0 %). Recrystallization from methanol/ether gives crystals of the hyirochloride as colorless plate. M.p.=225.0–231.0° C.

| Analysis (%) for $C_{19}H_{25}Cl_2N_3O_2.HCl$ |
|---|
| Calc.: C,52.32; H,6.00; N,9.77; Cl,24.54 |
| Found: C,52.49; H,6.03; N,9.66; Cl,24.46 |

IR (Nujol): 3303, 2635, 2575, 2538, 2507, 2420, 1713, 1619, 1541, 1483, 1462, 1442(sh), 1411, 1400, 1378.

NMR (CDCl$_3$) 1.52–1.90 (m, 6H), 1.90–2.15 (m, 4H), 2.35–2.55 (m, 1H), 2.435 (t, J=7Hz, 2H), 2.614 (t, J=8Hz, 2H), 3.036 (d, J=12Hz, 2H), 3.346, 3.409 (ABq, J=7Hz, 2H), 3.865 (t, J=7Hz, 2H), 7.044, 7.086 (ABq, J=2Hz, 1H), 7.345 (d, J=2Hz, 1H), 7.348 (d, J=8Hz, 1H).

The following Experiments have been conducted to demonstrate the pharmacological activities of the compounds of the present invention.

Experiment 1

(1) Evaluation of Effects on Neurotransmittal Systems {$^3$H} Serotonim (5-HT) Uptake Inhibition Test Test compounds Compound (a): a compound of the present invention
Compound (b): 1-[3-{4-(3,4-dichlorophenyl)-piperidin-1-yl}propylcarbamoyl]-2-oxopyrrolidin (Japanese Patent Publication (KOKAI) No.131155/1989).

Animals:

Male Slc: Wistar strain rats (12-week-old, Japan SLC).

Methods

Rats were killed by decapitation and a whole brain except for cerebellum is isolated immediately. The isolated tissue was homogenized in 20 volume of ice-cold 0.32 M sucrose solution by Potter-type homogenizer and centrifuged at 1,000× g for 10 min. The supernatant is centrifuged at 40,000× g for 20 min. The resultant pellet is resuspended in 20 volume of Krebs-Henseleit buffer containing 1 mM ascorbate, 0.17 mM EDTA and 0.08 mM pargyline by Polytron and centrifuged at 40,000× g for 10 min, which procedure was repeated two more times. The finally obtained pellet was resuspended in 20 volume of ice-cold Krebs-Henseleit buffer using Polytron. The resultant suspension was diluted to 1/10 with the same buffer to give a synaptosome sample.

A mixture of 5 nM [$^3$H]5-HT (10 μl), synaptosome sample (480 μl) and a solution (10 μl) containing a test compound at a predetermined concentration was incubated for 5 min at 37° C. The reaction was stopped by diluting the mixture with ice-cold Krebs-Henseleit buffer (2.5 ml) and filtering with suction on Whatman GF/C paper. The filter paper was washed three times with ice-cold Krebs-Henseleit buffer (2.5 ml each) and allowed to stand for about 18 hr in Cleasol-1 solution (5 ml). The radioactivity was then measured by means of a liquid scintillation counter. A control experiment was carried out in the same manner as the above using 5 nM [$^3$H]5-HT (10 μl), synaptosome sample (480 μl) and a solvent (10 μl) used for dissolving a test compound to obtain blank values of radioactivity.

The IC$_{50}$, the concentration of the test compound expressed in μM required to inhibit the uptake of [$^3$H]5-HT by 50%, was calculated from a graph on which the uptake of [$^3$H]5-HT by synaptosomes (radioactivity) is plotted on the ordinate and the concentration (in logarithm) of the test compound on the axis. Results are shown in Table 1 below.

TABLE 1

| Compound | IC$_{50}$ (μM) |
| --- | --- |
| Compound (a) | 0.13 |
| Compound (b) | 23.0 |

Table 1 shows that compound (a), the compound of the present invention, has much more potent serotonin uptake inhibitory activity compared to compound (b), a known compound, which demonstrates that the compound of the invention has an antidepressant activity.

(2) Evaluation of Effects on Cerebral Ischemia

Inhibitory effect against the delayed necrosis of hippocampus CAI pyramidal cells was determined.

Test compounds and Animals

Compound (a) and compound (b) were again used in this experiment. Three to eight male mice (Mongolian gerbil, 11 to 12-week-old, Seiwa Jikken-dobutsu Kenkyusyo) were used for one group.

Methods

Each animal was intraperitoneally administered a solution of the test compound (a) or (b) dissolved in distilled water, or only distilled water (for control) at 0.2 ml/100 g weight of the animal. Thirty minutes later, under the halothane anesthesia, bilateral common carotid artery was separated from surrounding tissues and ligated for a period of 5 min with Sugita's artery Klemme. Anesthesia was stopped at the time of artery occlusion. On the 4th day after the operation, each animal was anesthetized with pentobarbital Na (45 mg/kg), and brain was perfused with 4% paraformaldehyde solution and removed. From the brain was prepared a piece of cerebral preparation containing hippocampus. It was placed in Carnoy's fixative overnight for fixation and embedded in paraffin, from which sliced coronal preparations of 10 μm thick were prepared. Each cerebral preparation was stained with hematoxylin-eosin and the rate of injury (%) in pyramidal cell layer extending from paramedian to CA4 was observed using two-dimensional image analyzer (Cosmozon IS, Nicon). Results are shown in Table 2 below.

TABLE 2

| Dose (mg/kg) | Compound (a) | | Compound (b) | |
| --- | --- | --- | --- | --- |
| | injury (%) | inhibition (%) | injury (%) | inhibition (%) |
| 0 | 49.9 ± 1.6 | — | 45.2 ± 1.4 | — |
| 12.5 | 45.9 ± 2.1 | (+8.0) | 44.0 ± 3.2 | (+2.8) |
| 25.0 | 33.6 ± 5.3* | (+32.7) | 28.1 ± 8.3 | (+38.0) |
| 50.0 | 0 | (+100) | 30.7 ± 3.9** | (+32.1) |

*, p<0.05; and **, p<0.01, vs control

The table 2 above shows that compound (a), the compound of the invention, compared to compound (b), a known compound, significantly inhibited the delayed necrosis of hippocampus CAI pyramidal cells in mouse (Mongolian gerbil) due to the cerebral ischemia at the dosage of 12.5 and 25 mg/kg and completely inhibited at the dosage of 50 mg/kg.

(3) Enzyme Induction Test

Male mice (DS, 5–6 week-old) received intraperitoneally 100 mg/kg of the compound (a) of the present invention or the compound (c) (1-[3-}4-(3,4,-dichlorophenyl)-1,2,5,6-tetrahydropiperidin-1-yl}propylcarbamoyl]-2-oxopyrrolidine) suspended in 5% gum arabic once a day for three days. After 24 hrs from the final administration, the liver was removed from the animal, and liver microsome was prepared by means of centrifugal fractionation. Additional liver microsomes were prepared in the same manner as above by intraperitoneally administering a typical enzyme inducer, phenobarbital (dissolved in saline) or β-naphthoflavone (suspended in sesame oil), to mice. Enzymatic activities of the above liver microsomes on drug metabolism were evaluated by determining their 7-alkoxycumarin-O-dialkylase activities. The test results are shown in Table 3.

TABLE 3

| Test Compound | 7-alkoxycumarin-O-dialkylase activities (nmol/min/mg of microsome protein) | | | | | |
| --- | --- | --- | --- | --- | --- | --- |
| | demethylation activity | | deethylation activity | | depropylation activity | |
| Control | 2.58 ± 0.16 | (1.00) | 2.64 ± 0.22 | (1.00) | 1.21 ± 0.12 | (1.00) |
| Compound (a) | 2.79 ± 0.33 | (1.08) | 2.59 ± 0.27 | (0.98) | 1.08 ± 0.12 | (0.89) |
| Control | 1.13 ± 0.06 | (1.00) | 1.15 ± 0.05 | (1.00) | 0.45 ± 0.03 | (1.00) |
| Compound (c) | 1.83 ± 0.19* | (1.61) | 2.29 ± 0.18** | (1.99) | 0.99 ± 0.55** | (2.20) |
| Control | 0.95 ± 0.08 | (1.00) | 1.04 ± 0.01 | (1.00) | 0.48 ± 0.02 | (1.00) |
| phenobalbital | 2.18 ± 0.13** | (2.29) | 2.63 ± 0.18** | (2.53) | 1.06 ± 0.06** | (2.20) |
| β-naphtoflavone | 1.94 ± 0.08** | (2.04) | 5.26 ± 0.28** | (5.06) | 2.97 ± 0.20** | (6.19) |

*, p<0.05; and **, p<0.01, vs control

Apparent from Table 3, the mouse liver which received the compound (c) for three days increased its enzymatic activity on drug metabolisms. Specifically, demethylation activity increased 1.61 times, while deethylation and depropylation activities increased 1.99–2.20 times as compared with the control. Similar increasing pattern was also observed in the group treated with β-naphthoflavone, a typical enzyme inducer. On the other hand, the mouse liver which received the compound (a) showed substantially the same enzymatic activity on drug metabolism as the control. Thus, no enzyme induction was observed in the compound (a), while the compound (c) possesses a carcinogenic enzyme induction of β-naphthoflavone type (3-methylcholanthrene type).

As is understood from the test results given above, the compound of the present invention possesses a potent antidepressant activity and the inhibitory activity against the necrosis of neuronal cells, with less or negligible side effect of enzyme induction.

What is claimed is:

1. A compound of the formula (I):

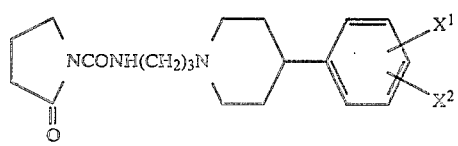

wherein $X^1$ and $X^2$ each independently represents lower alkyl, lower alkoxy or halogen or a pharmaceutically acceptable salt thereof.

2. A pharmaceutical composition for treating antidepressant, which contains as an active ingredient a compound as claimed in claim 1 together with a pharmaceutically acceptable carrier therefor.

3. A pharmaceutical composition for treating aftereffects of cerebrovascular impairments, which contains as an active ingredient a compound as claimed in claim 1 together with pharmaceutically acceptable carrier therefor.

* * * * *